(12) United States Patent
Drolet

(10) Patent No.: US 7,717,066 B2
(45) Date of Patent: May 18, 2010

(54) DEVICE FOR USE IN DETECTING DANGEROUS MATERIALS OR ILLEGAL SUBSTANCES IN SHIPPING CONTAINERS

(76) Inventor: Gerald Drolet, East Coast Ocean Villas, Unit 3C, 104/1 Moo 6, T. Pakhlok, A Thalang, Phuket (TH) 83110

( * ) Notice: Subject to any disclaimer, the term of this patent is extended or adjusted under 35 U.S.C. 154(b) by 168 days.

(21) Appl. No.: 12/002,702

(22) Filed: Dec. 19, 2007

(65) Prior Publication Data
US 2009/0162196 A1 Jun. 25, 2009

(51) Int. Cl.
*A01K 1/03* (2006.01)
(52) U.S. Cl. .................................................. 119/421
(58) Field of Classification Search ................ 119/421, 119/174; 15/347, 353; 73/23.43
See application file for complete search history.

(56) References Cited

U.S. PATENT DOCUMENTS

| | | | |
|---|---|---|---|
| 4,718,268 A | | 1/1988 | Reid et al. |
| 4,909,090 A | * | 3/1990 | McGown et al. ......... 73/864.33 |
| 5,195,209 A | * | 3/1993 | Watkins ...................... 15/339 |
| 5,739,412 A | * | 4/1998 | Stock et al. .................. 73/23.3 |
| 5,756,908 A | * | 5/1998 | Knollmeyer et al. ........ 73/866.5 |
| 5,818,059 A | * | 10/1998 | Coyne et al. .............. 250/507.1 |
| 5,859,362 A | * | 1/1999 | Neudorfl et al. ............... 73/23.2 |
| 6,185,782 B1 | * | 2/2001 | Hall ............................. 15/339 |
| 6,467,333 B2 | * | 10/2002 | Lewis et al. ................ 73/31.05 |
| 6,499,574 B1 | * | 12/2002 | Anthony ...................... 190/36 |
| 6,519,809 B2 | * | 2/2003 | Gutry ........................... 15/414 |
| 6,647,586 B2 | * | 11/2003 | Rogers et al. .............. 15/327.5 |
| 6,651,520 B1 | * | 11/2003 | Allen et al. .............. 73/863.81 |
| 6,766,560 B2 | * | 7/2004 | Murphy ........................ 15/414 |
| 6,823,714 B2 | | 11/2004 | Megerle |
| 7,550,022 B2 | * | 6/2009 | Smith ........................ 55/385.1 |
| 2003/0047700 A1 | * | 3/2003 | Motonaka et al. ........ 251/149.1 |
| 2004/0202574 A1 | | 10/2004 | Sapir et al. |
| 2008/0190376 A1 | * | 8/2008 | Matsumoto ................. 119/614 |
| 2009/0038555 A1 | * | 2/2009 | Reese .......................... 119/174 |

* cited by examiner

*Primary Examiner*—Rob Swiatek
*Assistant Examiner*—Ebony Evans

(57) ABSTRACT

A portable device for use in detecting dangerous materials and illegal substances in shipping containers with the aid of a trained dog. The device is used by a dog handler and constructed to be able to withdraw air from within a shipping container, through a high air vent in it's sidewall, and present the withdrawn air to the dog to smell. The dog is beside the handler on the ground beside the container when smelling the withdrawn air.

8 Claims, 2 Drawing Sheets

DEVICE FOR USE IN DETECTING DANGEROUS MATERIALS OR ILLEGAL SUBSTANCES IN SHIPPING CONTAINERS

BACKGROUND OF THE INVENTION

1. Technical Field

This invention is directed toward a portable device to be used in locating dangerous material and illegal substances in shipping containers. The device is to be used by a dog handler and his dog.

2. Background Art

Dangerous material or illegal substances such as explosives and drugs are often shipped into a country in shipping containers. The examination of shipping containers has always been difficult for any country's customs enforcement administration. The cost of examination is high and only a small percentage of the containers entering a country can be examined. Custom's enforcement personnel presently rely on intelligence information, expensive technology such as container x-ray systems, and labour intensive and time consuming manual inspections to try to minimize the entry of explosives and drugs into their country via shipping containers.

It is well known by custom's enforcement personnel to use dogs to detect dangerous materials or illegal substances such as explosives or drugs by smell. When the dogs are used to inspect shipping containers, it is necessary to unseal and open a shipping container to be able to have the dog inspect the container for explosives or drugs. Opening up a container for inspection by a dog however is time consuming and expensive.

SUMMARY OF THE INVENTION

It has been discovered that a small sample of air drawn from within a container through an existing air vent in the container and passed to a dog outside the container to smell, is sufficient for the dog to quickly tell if the material or substance the dog has been trained to detect is present within the container. The invention relates to a portable air sampling device used for obtaining the small air sample from within a closed container and positioning the sample for the dog to analyse.

The portable air sampling device can withdraw air from within the container through a high air vent commonly found on a sidewall of the container and direct it to a dog on the ground, beside the container, to smell. The sampling device is operated by the dog's handler. The device, which is light in weight, can be carried on the handler's hip supported by a shoulder strap. The sampling device has an inlet member at one end which is shaped to cover at least part of the vent in the container. The inlet member leads to a light weight conduit which leads to a small, battery operated, fan unit at the other end of the conduit. An outlet is provided from the fan unit for directing the air sample to the dog. An outlet member shaped to receive a dog's muzzle is preferably mounted to the outlet. The conduit is preferably rigid and telescopic.

In use, the handler locates a container to be searched on the ground and manipulates the device to position the inlet member over at least part of the vent on a sidewall of the container. The inlet member preferably has a seal member that bears against the vent to prevent mixing outside air with the air to be withdrawn from the container. Once the inlet member is positioned over the vent, the fan in the fan unit is operated to draw air from within the container and pass it through the vent, through the inlet member, and through the conduit to the fan unit. From the fan unit, the air is passed out of the outlet. The handler has the dog put his muzzle to the outlet to sniff the air passing from the outlet. The device is lightweight enough that the handler can position and operate the device while directing the dog to the outlet.

The invention is particularly directed toward a portable device for use in detecting dangerous materials and illegal substances in shipping containers. The device has a conduit with the conduit having an inlet member at one end, the inlet member shaped and sized to at least cover part of a vent on a sidewall of a shipping container. The conduit leads to a fan unit which has an outlet where a dog can smell an air sample taken from the shipping container. With the inlet member covering the vent opening, the fan unit is operated to draw air out of the container through the vent and the conduit to the fan unit and then out of the outlet.

DETAILED DESCRIPTION OF THE INVENTION

Figure 1:
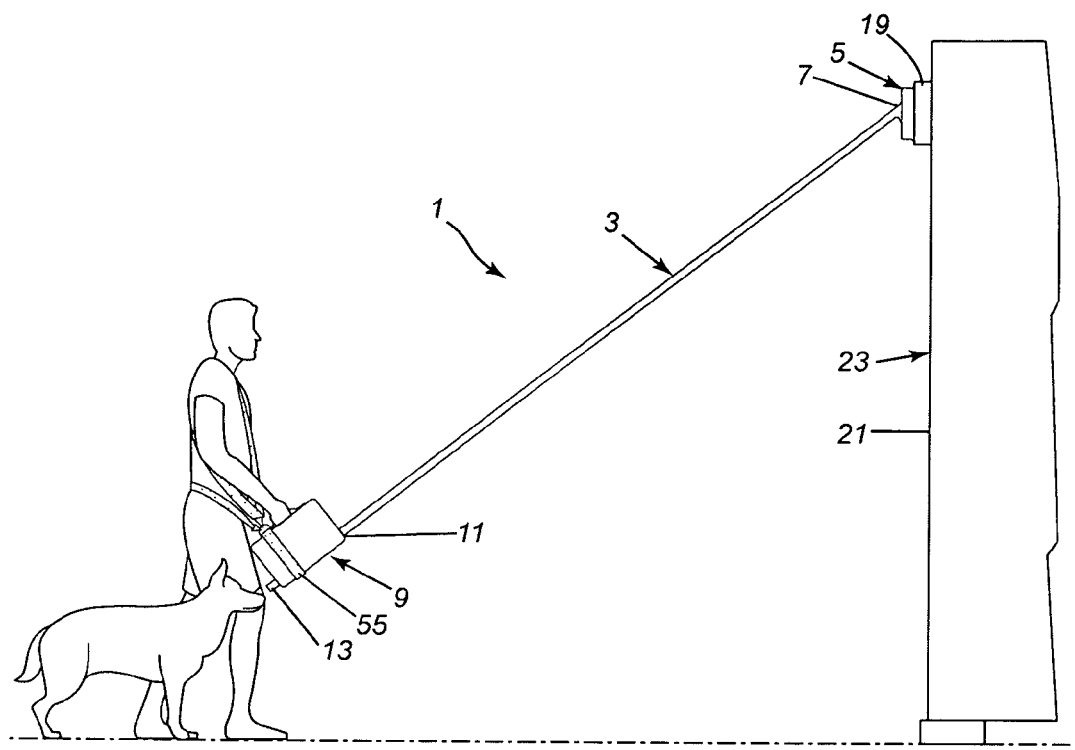
FIG. 1 is a side view of the portable sampling device in use.

The portable air sampling device 1, as shown in FIG. 1, has an air conduit 3 having an inlet member 5 at one inlet end 7 of the conduit 3, a fan unit 9 at the other outlet end 11 of the conduit 3 and an air outlet 13 on the fan unit 9.

Figure 2:
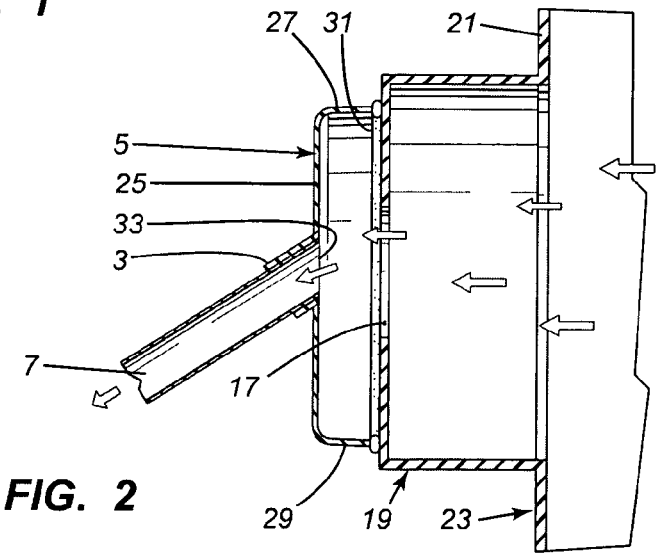
FIG. 2 is a detail cross-section view of the inlet member of the device.

The inlet member 5, as shown in FIG. 2, is sized to fit over a vent opening 17 in an air vent 19 on the upper portion of a sidewall 21 of a shipping container 23. The inlet member 5 has a back wall 25 and a sidewall 27 extending from the back wall 25 shaped to fit about the vent opening 17. The free edge 29 of the sidewall 27 can have a soft seal 31 attached thereon to abut the vent 19 encircling the vent opening 17. The seal 31 can be made of a polyurethane, such as visco-elastic polyurethane foam, or any other suitable air-sealing material. When the inlet member 5 is placed over the vent opening 17 in the vent 19 on the container 23 to have seal 31 on the edge 29 of its sidewall 27 abut the vent 19, it is sized to enclose the vent opening 17 in the vent 19. An inlet opening 33 in the back wall 25 of the inlet member 5 connects to the conduit 3. The vent opening 17 has been shown as a single opening but it usually comprises a cluster of small perforations in the outer wall of the vent 19. The inlet member 5 is sized to cover the cluster.

The conduit 3 is a rigid, light-weight, tube preferably made of aluminum, and preferably telescopic. The inlet end 7 of the conduit 3 is suitably attached to the back wall 25 of the inlet member 5. Preferably, the inlet member 5 is detachably connected to the conduit 3. A swivel connection (not shown) could be provided between the inlet member 5 and the conduit 3 to allow the inlet member 5 to swivel with respect to the conduit 3 so as to allow the inlet member 5 to be placed flush on the vent 19 irregardless of the angle the conduit 3 makes with the vent 19. The outlet end 11 of the conduit 3 can be fixedly or detachably connected to the fan unit 9.

Figure 3:
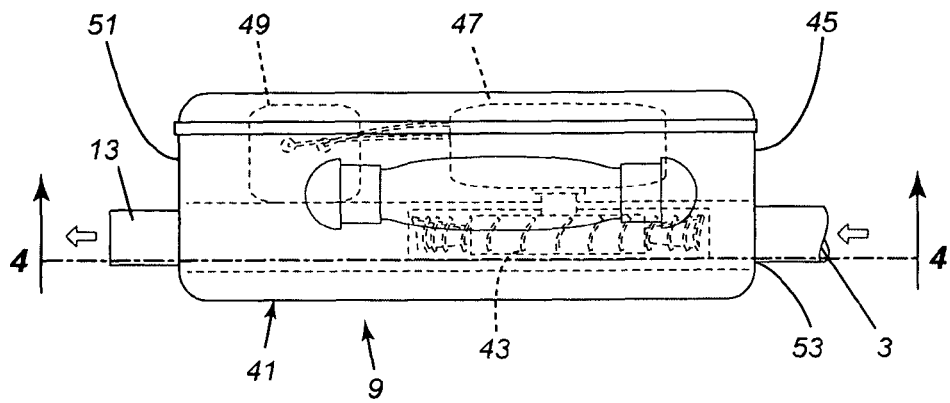
FIG. 3 is a detail top view of the fan unit.
Figure 4:
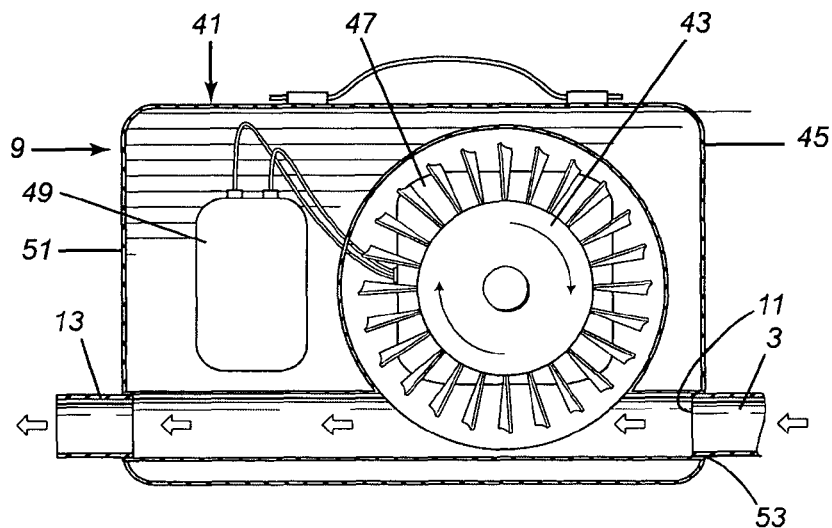
FIG. 4 is a cross-section view taken along line 4-4 in FIG. 3.

The fan unit 9, as shown in FIGS. 3 and 4, has a generally cylindrical, elongated, casing 41. A fan 43 is rotatably mounted within the casing 41 adjacent one end 45, the fan 43 operated by an adjacent motor 47. The motor 47 can be operated by a battery 49 located adjacent the other end 51 of the casing. The casing 41 has an inlet opening 53 at the one end 45 into which the outlet end 11 of the conduit 3 is suitably connected. The air outlet 13 is provided in the casing 41 at the other end 51 opposite the conduit 3. The fan 47 passes air from the conduit 3 through the casing 41 and out the air outlet 13. A harness 55 is preferably attached to the casing 41 of the fan unit 9, the harness 55 carrying a belt and a shoulder strap for use by the handler in carrying the device.

In use, the dog handler positions the inlet member 5 of the device 1 over a the vent opening 17 in a vent 19 on a container 21 to be checked for dangerous material or illegal substances and then starts the fan 47 in the fan unit 9 with a switch (not shown). The fan 47 operates to withdraw air from within the container out through the vent opening 17, through the conduit 3, and out the air outlet 13. While manipulating the device 1 to keep the inlet member 5 against the vent 19 covering the vent opening 17, the handler has the dog place his snout to the air outlet 13 to smell the air obtained from the container.

Figure 5:
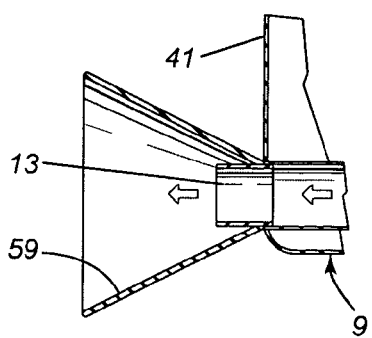
FIG. 5 is a detail cross-section view of the outlet member of the device.

To obtain a more concentrated air sample for the dog to smell, the air outlet 13 is preferably provided with an outlet member 59 shaped to receive the muzzle of the dog. The outlet member 59, as shown in FIG. 5, has a relatively truncated, cone shape. The outlet member 59 can be made from leather or a suitable moldable, plastic material that is flexible yet stiff enough to generally retain its shape. The outlet member 59 can be attached directly to the casing 41, or to a short conduit (not shown), rigid or flexible, leading from the air outlet 13 in the casing 41.

Figure 6:
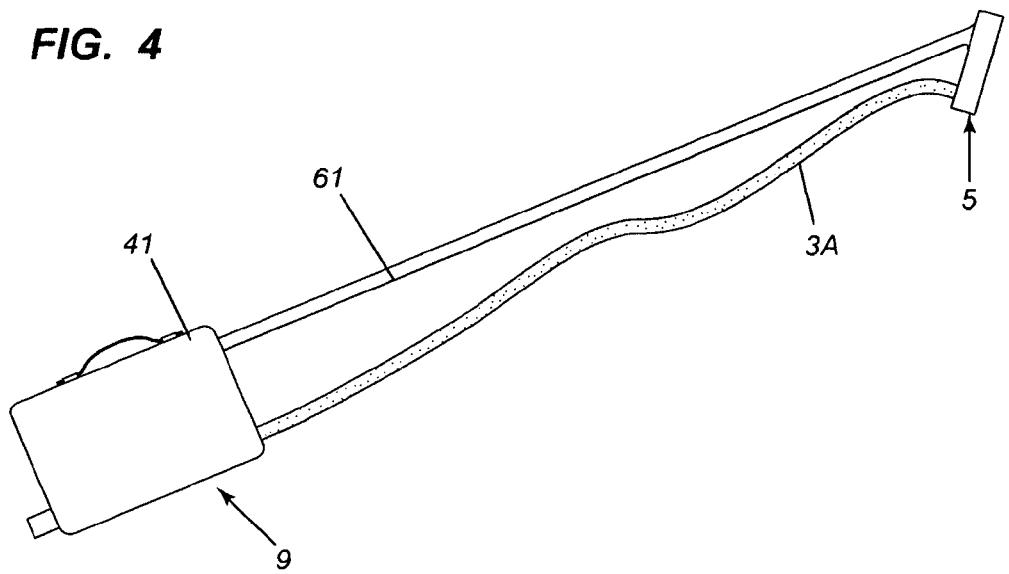
FIG. 6 is a side view of another embodiment of the sampling device.

The conduit 3 has been described as being rigid. It could however be flexible as shown by conduit 3A in FIG. 6. A rigid rod 61 can be attached between the casing 41 and the inlet member 5 to support the inlet member and the attached conduit 3A. The rod 61 could be made adjustable in length or its point of attachment on the casing 41 could be varied to adjust its operative length.

If desired, the casing 41 can carry a tripod(not shown) on its bottom which could be opened up to support the fan unit 9, and thus the device, on the ground while the air sample is being taken. Different sized inlet members 5 could be used to match different sized vent outlets 17 on the container, the members being easily changeable. The inlet members 5 have been described as having a seal made from a soft sealing material. The outlet member 5 could however be made in one piece from the sealing material. The outlet member 5 has also been described as being sized to enclose a vent opening on a vent. The outlet member 5 could however also be sized to enclose the entire vent 19, bearing against the sidewall 21 of the container instead of on the vent. Different sized outlet members 59 could also be used to match the muzzle size of the dogs being used so that the dog's muzzle has a snug fit with the outlet member 59.

I claim:

1. A portable device for use in detecting dangerous materials and illegal substances in shipping containers, the device comprising: a conduit; the conduit having an inlet member at one end, the inlet member shaped and sized to cover at least part of an air vent on a sidewall of a shipping container; a fan unit at the other end of the conduit for drawing an air sample out of the container through the vent, the inlet member and the conduit to the fan unit when the inlet member covers the air vent; a rigid member directly connecting the inlet member to the fan unit, the rigid member being long enough to be able to have a person, standing on the ground next to the shipping container with the fan unit, position and hold the inlet member over the air vent with the rigid member while taking the air sample; and an outlet from the fan unit for passing the air sample.

2. A portable device as claimed in claim 1 wherein the device is filterless and the outlet from the fan unit carries a shaped outlet member, shaped to receive the muzzle of a dog.

3. A portable device as claimed in claim 2 wherein the device is filterless and includes carrying means on the device to allow the person to carry the device with his body with the outlet in a position to be accessible to the dog and with his hands free to manipulate the inlet member.

4. A portable device as claimed in claim 3 wherein the inlet member is sized to cover the vent while bearing on the sidewall of the container.

5. A portable device as claimed in claim 2 wherein the inlet member is sized to cover the vent while bearing on the sidewall of the container.

6. A portable device as claimed in claim 1 wherein the device is filterless and includes carrying means on the device to allow the person to carry the device with his body with the outlet in a position to be accessible to a dog and with his hands free to manipulate the inlet member.

7. A portable device as claimed in claim 6 wherein the inlet member is sized to cover the vent while bearing on the sidewall of the container.

8. A portable device as claimed in claim 1 wherein the inlet member is sized to cover the vent while bearing on the sidewall of the container.

\* \* \* \* \*